|   |   |
|---|---|
| United States Patent [19] | [11] 4,312,734 |
| Nichols | [45] Jan. 26, 1982 |

[54] ION-SELECTIVE ELECTRODE

[75] Inventor: Michael F. Nichols, Columbia, Mo.

[73] Assignee: The Curators of the University of Missouri, Columbia, Mo.

[21] Appl. No.: 122,370

[22] Filed: Feb. 19, 1980

[51] Int. Cl.³ .............................................. G01N 27/36
[52] U.S. Cl. ................................. 204/195 G; 128/635
[58] Field of Search ................... 204/195 G; 128/635; 324/438

[56] References Cited

U.S. PATENT DOCUMENTS

| 2,422,628 | 6/1947 | McCarthy | 117/53 |
|---|---|---|---|
| 3,498,901 | 3/1970 | Metz et al. | 204/195 G |
| 3,673,069 | 6/1972 | Niedrach et al. | 204/195 G |
| 3,718,569 | 2/1973 | Petersen et al. | 204/195 G |
| 3,923,625 | 12/1975 | Fischer et al. | 204/195 G |
| 3,959,106 | 5/1976 | Horner et al. | 204/195 G |
| 3,973,555 | 8/1976 | Möller | 128/635 |
| 4,012,308 | 3/1977 | Jerrold-Jones et al. | 204/195 F |
| 4,031,606 | 6/1977 | Szonntagh | 29/570 |
| 4,133,735 | 1/1979 | Afromowitz et al. | 204/195 G |

OTHER PUBLICATIONS

Josef Vesely et al., "Analysis with Ion–Selective Electrodes", pp. 46–48, (1978).
M. R. Thompson, Bureau of Standards Journal of Research, vol. 9, pp. 833–853, (1932).
Sydney M. Friedman et al., Proc. Soc. For Experimental Biology & Medicine, 99;727, (1958).

*Primary Examiner*—G. L. Kaplan
*Attorney, Agent, or Firm*—Senniger, Powers, Leavitt and Roedel

[57] ABSTRACT

A dry glass electrode for use in potentiometric analyses of aqueous media. The electrode comprises a metal conductor constituted of platinum, gold, or tantalum, a layer comprising an oxide of the metal having a thickness of between about 50 Angstrom units and about 2 microns on an outer surface of the metal conductor, and an ion-selective glass membrane over and in electrical contact with the oxide layer. The ion-selective glass has a coefficient of thermal expansion differing by less than about 25% from the coefficient of thermal expansion of the metal.

A method for producing the electrode of the invention is also disclosed.

10 Claims, 9 Drawing Figures

10mm = 1cm

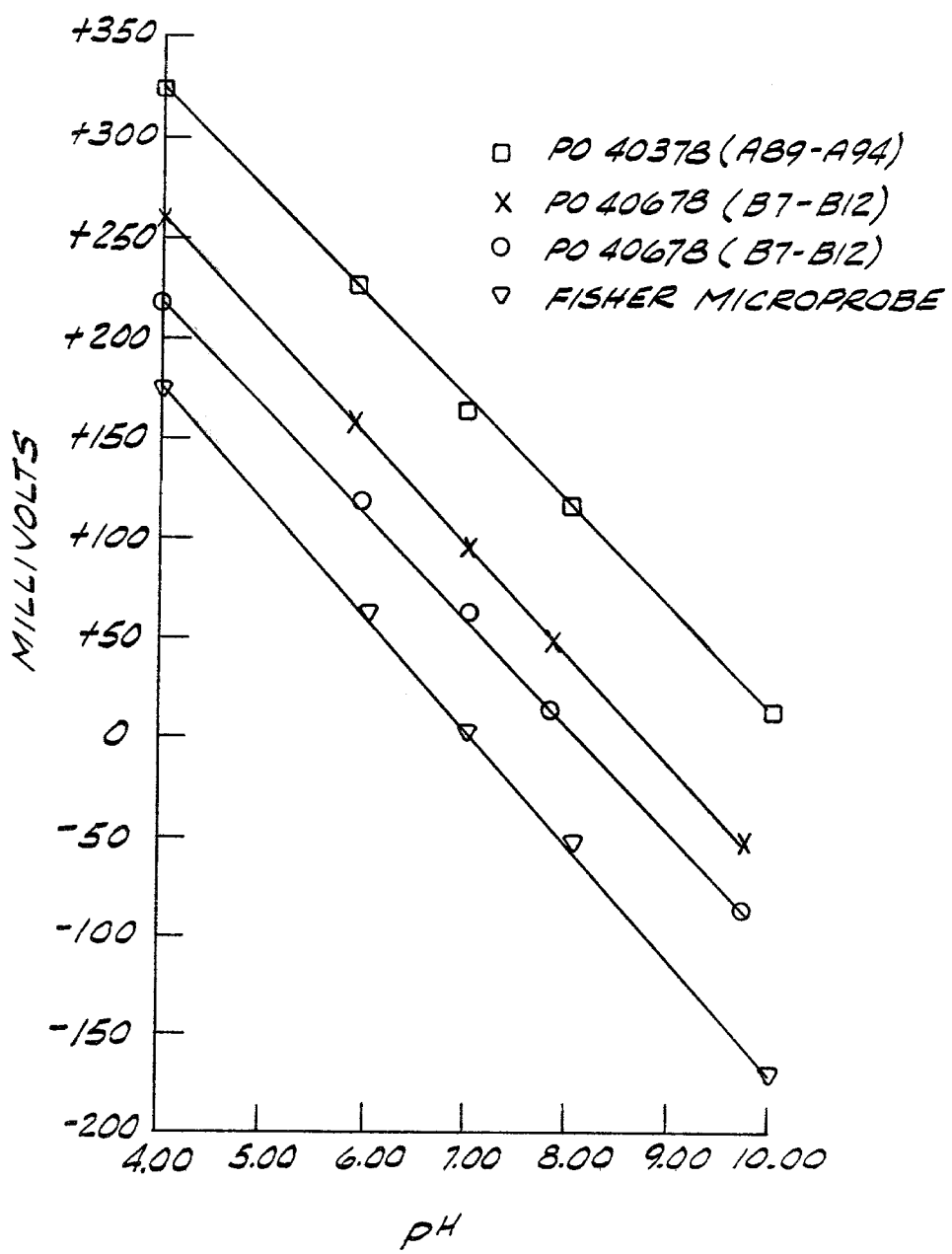

ION-SELECTIVE ELECTRODE

BACKGROUND OF THE INVENTION

This invention relates to the field of concentration measuring elecrodes and more particularly to an improved solid state electrode for use in potentiometric analyses and a novel method for the preparation thereof.

A variety of chemical indicators are available for measurement of the pH of aqueous media, but the most accurate, precise and reliable pH measurements are generally recognized to be those taken potentiometrically. In potentiometric analysis for pH, an electrometer, potentiometer or other voltage measuring device is utilized to measure the difference in potential between a special pH electrode immersed in the aqueous medium to be tested and a reference electrode that is in electrical communication with the same aqueous medium typically through a potassium chloride salt bridge. The pH electrode is one whose potential varies as a function of the hydrogen ion concentration of the aqueous medium, generally in accordance with the classical Nernst equation. The reference electrode is typically calomel or Ag/AgCl electrode, with the latter being preferred for physiological applications.

By suitable selection of measuring electrodes, concentration cells can be established for measurement of a variety of different ions. Potentiometric analysis can also be utilized for the determination of the equilibrium coefficients for various acid dissocation reactions or other ionic reactions in aqueous media.

For measurement of pH, it has long been conventional to use a glass electrode as the measuring electrode. The standard glass electrode includes a hollow bulb constructed of special ion selective glass, which serves as a membrane for charge transfer in response to the concentration of hydrogen ions in the medium to be measured. Contained within the glass bulb is a solution in which is immersed a standard electrode such as an Ag/AgCl electrode. A large variety of shapes and sizes of this basic electrode type, including micropipette, capillary, etc. have been fabricated. However, such "wet connection" electrodes are of limited utility in certain applications, including service under extremes of pressure and/or temperature and important physiological applications where small size is critical. In the present state of the art the minimum size attainable in a conventional wet connection glass electrode is a diameter about 1.5 mm for the bulb containing the internal electrode. Although micropipettes can be constructed in diameters smaller than this at their tips, they are unsuitable mechanically for muscular implant and intravascular use.

In the present state of technology, the glass bulb of a wet connection pH electrode must be made with a certain minimum thickness for adequate mechanical strength which, in combination with the relatively small area of the bulb, results in a relatively high impedance and increases both the response time of the electrode and the shielding required. Moreover, the response characteristic generally shifts with age due to alteration of the glass charge transfer properties through hydration by the internal solution. The wet connection pH electrode is also relatively fragile, difficult to reproduce consistently in small sizes by the necessary process of glass blowing, and subject to operation only within a relatively limited temperature range because of the generation of internal pressure.

In order to overcome some of the difficulties associated with conventional wet connection glass electrodes, proposals have been made for the use of solid state electrode for pH measurement. Such were first proposed by M. R. Thompson, Journal of Research National Bureau of Standards, Vol. 9 p. 833 (1932) and pioneered by Friedman et al. Proceedings of The Society of Experimental Biological Medicine Vol. 99 p. 727 (1958). However, successful work with solid state electrodes has been largely limited to capillary (flow through) electrodes, wherein metal is applied to the outside of a glass tube through which the medium to be measured is caused to flow. The art has encounterd considerable difficulty in developing a feasible method for the production of dip-type solid state glass electrodes, in which a metal conductor is contained within an ion-selective glass envelope or membrane.

Recent developments in solid state glass electrodes are described in Metz et al. U.S. Pat. Nos. 3,498,901 and Szonntagh 4,031,606. Metz et al. describe a glass electrode having a superficially oxidized copper connection with a thin overlayer of glass that is fused to the oxidized surface through partial diffusion of the oxide into the glass. Szonntagh describes a laminate electrode having stacked layer of glass, silver chloride and silver encapsulated in a potting compound. From his patent disclosure, it would not appear that the Szonntagh electrode is adapted for production in such dimensions and configurations as to be suitable for critical physiological uses.

SUMMARY OF THE INVENTION

Among the several objects of the present invention, therefore, may be noted the provision of an improved solid state glass electrode for use in potentiometric analyses; the provision of such an electrode which maintains high stability with age; the provision of such an electrode which is adapted for miniaturization and physiological application; the provision of such an electrode which exhibits a low impedance and affords a rapid response; and the provision of such an electrode which does not require extensive shielding.

Additional objects of the invention include the provision of a novel and advantageous method for the production of solid state glass electrodes; the provision of such a method which reproducibly provides dry electrodes of high quality; the provision of such a method which facilitates quality control without demanding highly skilled labor; the provision of such a method through which high quality solid state glass electrodes can be made with high productivity; and the provision of a method for producing novel solid state electrodes having the characteristics referred to hereinabove.

The present invention, therefore, is directed to a dry glass electrode for use in potentiometric analyses of aqueous media. The electrode comprises a metal conductor constituted of a metal selected from the group consisting of platinum, gold, and tantalum. A layer comprising an oxide of said metal having a thickness of between about 50 Angstrom units and about 2 microns is on the outer surface of the metal conductor. Over and in electrical contact with said oxide layer is an ion-selective glass membrane having a coefficient of thermal expansion differing by less than about 25% from the coefficient of thermal expansion of the metal.

The invention is further directed to a method for preparing a solid state glass electrode having an ion-selective alkali metal-containing glass membrane over a surface-oxidized metal conductor. In this method, a platinum or gold conductor is electrolytically etched in an alkaline solution containing cyanide ions and ions of the principal alkali metal of the ion-selective glass. An etched surface of the conductor is oxidized; and an etched surface-oxidized portion of the conductor is covered with an ion-selective alkali metal-containing glass. The conductor and glass are heated to a temperature sufficient to form a membrane of glass over said portion and heat-seal said glass to the metal oxide layer to provide an electrically conductive junction therebetween. The glass is annealed by cooling at a rate which substantially avoids phase separation in the glass.

Other objects and features will be in part apparent and in part pointed out hereinafter.

BRIEF DESCRIPTION OF THE DRAWINGS

FIG. 9 is a graph showing calibration curves for certain pH electrodes made in accordance with the working examples.

Corresponding reference characters indicate corresponding parts throughout the several views of the drawings.

DESCRIPTION OF THE PREFERRED EMBODIMENTS

In accordance with the present invention, a unique method has been discovered for producing a novel solid state glass electrode that has excellent performance properties and is adapted for physiological use. The method facilitates the production of miniaturized glass electrodes which are small enough for use in such specialized applications as intravascular catheters, yet strong enough for use in muscle implants. The method of the invention does not demand highly skilled labor, yet affords reliable and reproducible high productivity manufacture of solid state electrodes. The electrode of the invention exhibits rapid response, requires minimal shielding and maintains a constant potential characteristic that does not shift materially with the age of the electrode.

In carrying out the method of the invention, discrete conductor elements are provided, preferably of metal wire. A surface of each conductor that is to serve as an electrochemically active part of the electrode is electrolytically etched in an alkaline cyanide solution whose predominant cations are the same as those of the alkali metal of the later-applied glass membrane. Thereafter, the etched surface of the conductor is oxidized, preferably anodically. The etched and oxidized surface is covered with ion-selective glass and the conductor and glass are heated to provide a seal and then cooled to anneal the glass.

As noted, the conductor element of the electrode is preferably of wire. For the physiological applications for which the electrode of the invention is particularly adapted, the wire conductor should be very narrow gauge for example 100-500 in diameter. Prior to etching, the conductor is cleaned, conveniently by sequential application of methyl alcohol and distilled water.

Figure 3:
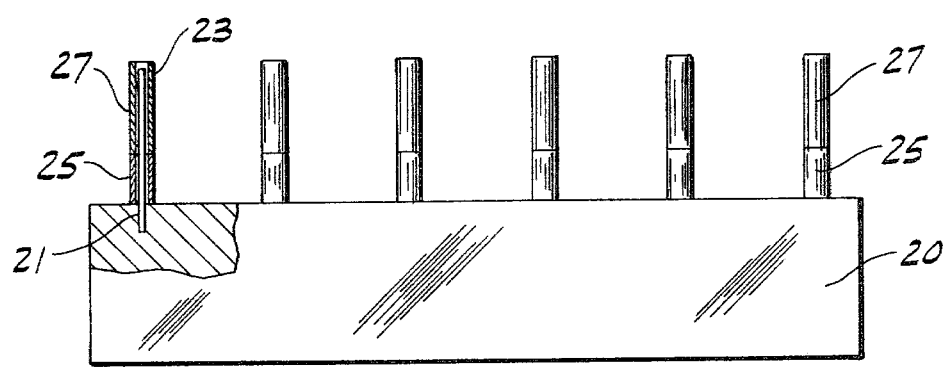
FIG. 3 illustrates an assembly of lengths of wire and surrounding glass tubes carried by a holder and ready for placement in a heat-sealing and annealing oven in accordance with the method of the invention.

The etching step of the process is of critical importance in preparing the conductor surface for effective bonding and electrical contact with the subsequently applied glass membrane. A system for carrying out the etching operation is shown in FIG. 3. A wire 1 to be etched, for example of platinum, gold, or tantalum, is immersed in an etching bath 3 contained within vessel 5. Wire 1 is electrically connected to one terminal of an A.C. voltage supply while the other terminal is connected to an inert electrode 7 that is also immersed in bath 3. The power supply is connected to an A.C. line voltage source 9 and comprises a tapped autotransformer 13 and a step-down transformer 15. Voltage between the electrodes is measured by a voltmeter 17 and electrolytic current by an ammeter 19.

Where wire 1 is constituted of platinum or gold etching bath 3 is a strongly basic solution containing cyanide ions and ions of the principal alkali metal of the glass that is used for the subsequently applied membrane. Preferably, the solution is between about 6 M and 12 M in cyanide ions with a concentration of about 7.5-8.0 M being about optimal. In order to suppress HCN formation the alkali hydroxide should be present in a proportion of at least about 1.5 mole per mole CN-. For best results in the etching step, the pH should be in the neighborhood of 11.

Etching is preferably carried out at a voltage of between 1 and about 12 volts at an amperage of between about 0.001 and about 3.0 amps. In accordance with the invention is has been discovered that, by proper scheduling of voltage, a hemispherical configuration rather than a point can be generated on the tip of the etched end of the wire. This result may be achieved by gradually stepping down the voltage from an initial voltage of about 5–10 v. to a finishing voltage of about 1 v. Advantageously, the wire electrode is repetitively dipped into and removed from the electrolytic etching solution at each voltage, thus alternately opening and closing the circuit, through 40-75 cycles. For a 100$\mu$ diameter platinum wire immersed a distance of 1.5 to a 2 mm in the etching solution, a hemispherical tip can be generated, for example, by progressively reducing the voltage from about 6 v. to about 1 v. in three to four steps, carrying out 50-60 cycles at each step, with the electrode immersed in the solution for about 30 seconds and then removed from the solution for about 30 seconds in each cycle. A hemispherical tip is preferred since it causes the glass membrane subsequently formed thereover to also be hemispherical, thus reducing the effects of the asymmetry potential that is developed on pointed electrodes.

Where the wire conductor is constituted of tantalum a sodium bromide etching solution is used and conditions are adjusted to produce a hemispherical tip on the tantalum wire etched in the bromide medium.

As a result of the etching process, the etched surface of the conductor is adapted for effective oxidation and application of the glass membrane. It has further been observed that the etched surface contains minute amounts of the principal alkali metal of the etching solution alloyed with the metal of the conductor at said surface. Although I do not wish to be bound to a particular theory, it is believed that the presence of this metal provides a source of alkali metal for migration to and replenishment of alkali metal that is driven off from the internal glass surface when the glass is heated for sealing. Maintenance of alkali metal at the glass/metal oxide interface is essential to facilitate charge transfer between the glass and the metal and thereby minimize the impedance of the electrode and improve its response. It is theorized that charge transfer proceeds along alkali metal ion channels within the glass membrane.

The presence of sodium at the glass metal/oxide interface has also been found to promote adherence of the glass to the metal. Adherence is further enhanced by the increase in surface area afforded by the etching process.

After removal of the wire from the etching bath, the etched end thereof is rinsed in deionized water. Thereafter at least a portion of the etched surface is oxidized to provide a layer of oxide on the outer surface of the conductor to which the glass membrane can be joined. Of the metals suitable for use in the conductor, platinum is fairly readily subject to formation of a stable surface oxide layer on heating in air. As one alternative, therefore, the oxide layer on a platinum wire may be formed in the furnace in which the wire is heated for sealing to the glass membrane. For gold and tantalum (and optionally for platinum) the oxide layer is provided by anodization of the etched surface. In the anodization step, the etched end of the wire is immersed in an acid solution and connected to the positive terminal of a direct current power source whose negative terminal is connected to an inert cathode also immersed in the acid. The acid solution is preferably sulfuric acid, for example 1N, in which effective anodization can be carried out at 1–3 volts in about 10–20 minutes, producing an oxide layer having a thickness on the order of about 100–1000 Angstrom units. However, other suitable acids such as oxalic acid may also be used. Chromic acid is not preferred because of the possible alteration of the electrical properties of the conductor. An oxide layer as thin as about 50 Angstroms is effective for subsequent bonding of an ion-selective glass membrane to the oxide layer. To minimize impedance and leakeage currents of the electrode, the oxide layer should not be thicker than about $2\mu$.

After the anodization step is complete the oxidized surface is rinsed in deionized water and dried. The surface is then in desired condition for application of the glass member thereover.

Figure 5:
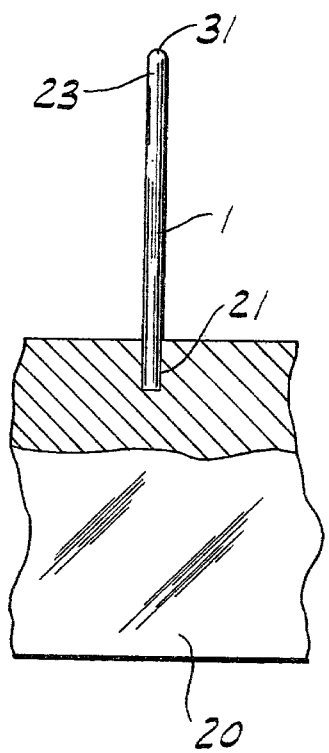
FIGS. 5-7 are views illustrating the process of preparing assemblies of wire conductors and glass tubes on a holder of the type shown in FIG. 3 and thereafter heat treating to seal a glass membrane over the tip of the conductor.
Figure 6:
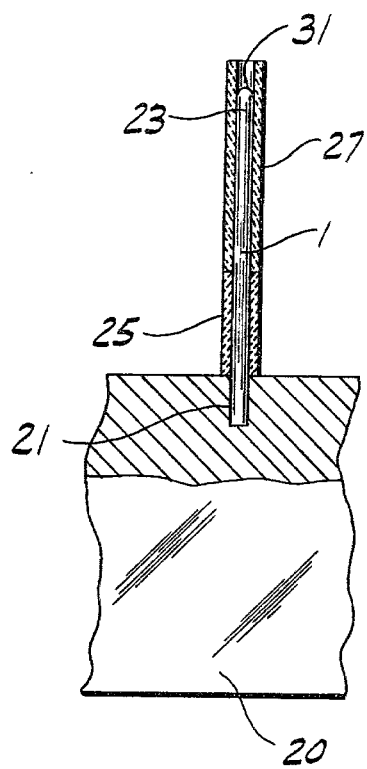

In a preferred procedure for carrying out the heat treatment steps of the method of the invention, as illustrated in FIG. 3 and 5–7, a ceramic block holder 20 is provided having in the upper surface thereof a number of cylindrical wells 21. The block is constituted of a glass ceramic material such as Macor that does not serve as a source of interfering ions that could migrate into the glass membrane. Lengths of wire 1 that have been subjected to the etching and anodizing operations described above are inserted vertically into wells 21, with the etched and anodized ends 23 thereof uppermost (FIG. 5). A cylindrical sleeve 25 constituted of an insulating glass is slid over each length of wire 1 so that it rests on the upper surface of block 20 (FIG. 6). Sleeve 25 is of such length as to leave the upper end of the wire exposed. A tube or sleeve 27 of ion-selective glass is placed over the upper end of wire 1 abutting sleeve 25 and supported thereon. Tube 27 is of a length sufficient so that the top thereof extends above the top of the wire.

The constituent ion-selective glass of tube 27 has a coefficient of thermal expansion which differs by less than about 25% from the coefficient of thermal expansion of the metal constituting wire 1. Preferably, the insulating glass of sleeve 25 also has a coefficient of expansion of the same order of magnitude as that of wire and ion-selective glass.

The block holder carrying the wire and glass sleeve assemblies is placed in an oven and heated to a temperature at which plastic flow of the glass occurs so that glass tube 27 closes at its upper end. The ion-selective glass seals over the upper end 23 of the wire to form membrane 27A (FIG. 2.) which bonds to the metal oxide layer at that end, thereby forming an electrically conductive junction between the oxide layer and the glass. At the same time, the abutting ends of ion-selective glass tube 27 and insulating glass sleeve 25 become fused together, both the glass members adhere to the surface of the wire, and the insulating glass forms an insulating jacket 25A surrounding wire 1. The bond formed between membrane 27A and the metal oxide layer is effective to provide a low impedance electrical junction between the glass and wire. Because of the vertical orientation of the wire, the effect of gravity causes flow of glass during heat-sealing so that glass membrane 27A is very thin and exhibits a relatively low impedance.

The temperature required for heat-sealing is a function of the glass composition and is readily determined by routine testing. For a typical soda/lime base ion-selective glass, sealing may be accomplished by heating to a temperature of approximately 880°–940° C. A relatively high sealing temperature causes a relatively low glass viscosity to be achieved and consequently provides a very thin low impedance glass membrane at the oxidized upper end of the wire. However, the sealing temperature should not be so high that the glass is caused to form a thin liquid that runs down the side of the wire. Also, excessive temperature may cause the loss of $Na^+$, sodium oxide (by vaporization) thus resulting in poor adherence of the glass to the metal and nonuniform coating of the surface.

After sealing is achieved, the electrode thereby produced is cooled at a controlled rate to anneal the glass and maximize its mechanical strength. By annealing under proper conditions, phase separation in the glass is avoided, resistance of the membrane is maintained at approximately 10 to $100 \times 10^6$ ohms, and the breaking stress of the glass is increased two to three times normal for thin ($<15\mu$) membranes. If the glass is annealed too slowly it is believed that the sodium ion channels for charge transfer are obstructed or lost. If annealing is carried out at an optimum rate, the glass acquires mechanical properties of an elastic character. Satisfactory annealing is achieved if the glass is cooled at a rate of between about 10 and about 25° C. per minute to a temperature just above the softening point (e.g., 625°–675° C. depending on the composition of the glass), thereafter at a rate of between about 4 and about 6° C. per minute to a few degrees above the annealing point (475°–525° C.), and thereafter at a rate of between about 1° and 4° C. per minute to the strain point. The rate of cooling in the last stage largely governs the offset potential and sensitivity of the electrode. For maximum sensitivity, the glass should not be maintained above the annealing point for more than about 15–20 minutes. If it is, the resistance of the electrode can be increased two to three times, and its sensitivity correspondingly decreased, for example, from a normal 55–60 mv/pH unit to 25–30 mv/pH unit.

Figure 1:
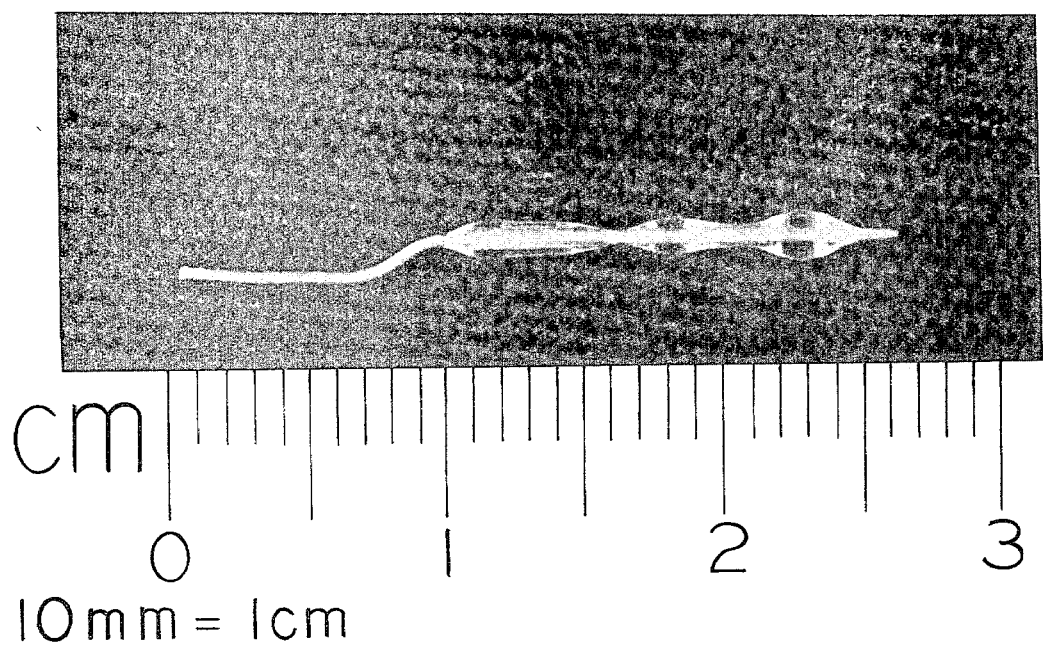
FIG. 1 is an enlarged photograph of the electrode of the invention indicating its dimensions.
Figure 2:
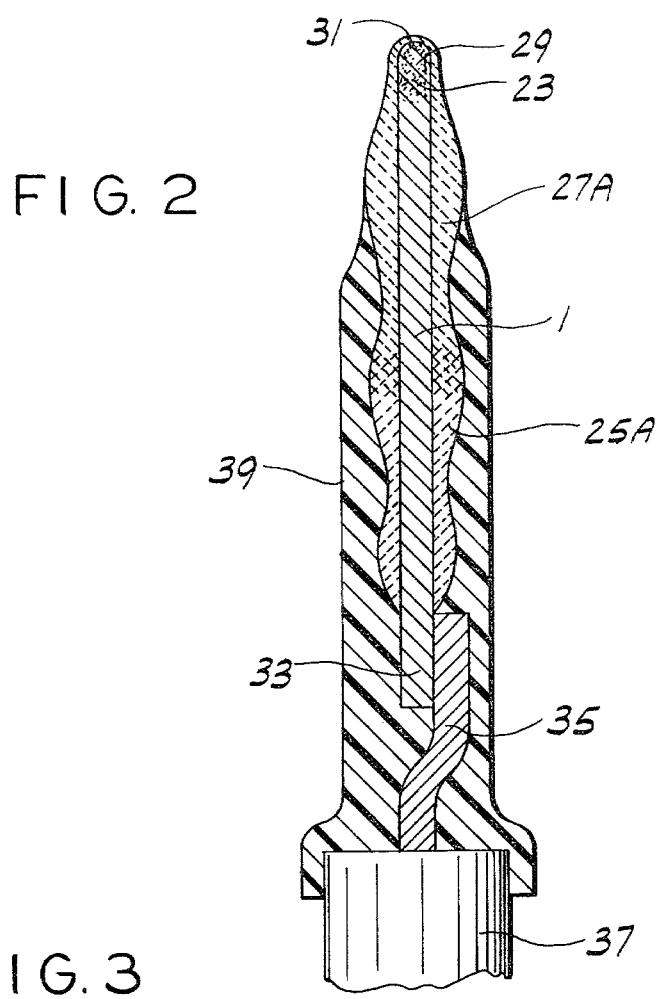
FIG. 2 is a longitudinal section drawing of the electrode of the invention indicating its component structural features.

FIG. 1 of the drawings is an enlarged photograph showing typical dimensions of an electrode of the invention, while FIG. 2 is a longitudinal sectional drawing of the electrode of FIG. 1. As shown in the drawings, the electrode can be produced in miniature sizes which are adapted for physiological applications, particularly in such specialized services as intravascular catheters and muscle implants. As illustrated in FIG. 2 the electrode comprises a wire conductor 1, of platinum, gold, or tantalum which is etched at one end 23 thereof and bears an oxide layer 29 extending along the outside of the wire from a hemispherical tip 31 at end 23. Metal oxide layer 29 has a thickness of between about 50 Angstroms and about 2 microns, preferably 100–1000 Angstroms. Alkali metal from the etching solution is entrapped as sodium oxide in the oxide layer and at the interface of the oxide layer and the interior of wire 1 in the region of tip 31. Over and in the low impedance electrical contact with layer 29 is ion-selective glass membrane 27A. Glass insulating jacket 25A is fused to membrane 27A and surrounds a portion of wire 1 spaced longitudinally from tip 31. End 33 of the wire opposite from tip 31 extends beyond glass jacket 25A and is joined to a lead wire 35, for example, by a silver epoxy adhesive. Lead wire 35 is in turn electrically connected to other elements of a potentiometric circuit (not shown) through a low noise miniature coaxial cable 37. A coating 39 of polymeric plastic insulative (potting) material covers the lead wire and entire electrode except for the membrane over tip 31 which is left exposed. This relatively thin polymer coating provides R.F. shielding for the electrode.

As indicated in FIG. 1, the electrode of the invention can be produced in miniature, having, for example, a total length of 25 mm with a sensing portion extending only a few millimeters from the membrane-enclosed tip. A particular advantage of the invention is the capability for producing electrodes of very small diameter, for example 100 to 500μ, and having low impedance glass membranes of thickness 5 or less. Because the metal oxide/glass interface acts somewhat like a diode, D.C. resistance is a function of polarity. However, at 1 KHz A.C. the reactance is typically 30–50×103 ohms and the capacitance 100–5000 pf.

Low impedance contributes to miniaturization of the electrode assembly, inasmuch as the shielding required to eliminate noise and stray currents is comensurately reduced. Not only is the extent and size of the shielding minimized but the low impedance of the glass membrane permits adequate shielding to be provided with resin coatings such as epoxy, which are not adequate for shielding of conventional glass electrodes having relatively thick glass membranes.

Another consequence of the low impedance of the membrane is rapid response of the electrode to changes in ion concentration in the solution being measured. The solid state junction between the conductor and the glass also contributes to rapid response since, unlike the case of conventional wet glass electrodes, diffusion operates to limit the rate of response only on one side (the outside) of the membrane.

Another important advantage of the electrode of the invention is its stability against change in response with age. In a conventional wet glass electrode, the glass membrane deteriorates due to the effect of the internal solution altering the slope of the voltage vs. concentration and response curve. In the electrode of the invention there is no internal solution and, since the electrode is stored out of contact with any aqueous medium, stability and reproducibility are maintained.

As noted, a factor which is believed to contribute materially to the low impedance of the electrode of the invention is the presence of the principal alkali metal of the etching solution as sodium oxide at the etched surface of the metal. Typically the predominant alkali metal ion in both the etching solution and the subsequently applied glass membrane is sodium. The presence of sodium at the etched surface provides a sodium "pool" which is believed to maintain sodium "channels" in the glass to provide paths of charge transfer which minimize the impedance of the glass membrane and the glass/metal junction. Alkali metal oxide further serves to promote the adherence of the glass to the metal. When present in sufficient amounts, as provided by etching in accordance with the method of the invention, the alkali metal at the conductor surface thus promotes charge transfer and contributes to low impedance. It may also be postulated that the electrode operates by a capacitance effect, whereby charges established at the outer membrane surface by ions for which the glass is selective induce opposite charges in the immediately adjacent glass surface and in turn cause a charge of the polarity of the selected ions to migrate to or be induced at the glass/metal oxide interface, from whence it can be communicated to measuring instruments. Where the oxide layer is produced by anodization it has further been discovered that minimum leakage currents are experienced so that the aforesaid capacitance effect is promoted. However, regardless of the exact half cell mechanism of the electrode in a particular solution, it has been demonstrated that the method of the invention produces an electrode which is uniquely responsive and effective for physiological applications.

The following examples illustrate the invention:

EXAMPLE 1

Figure 4:
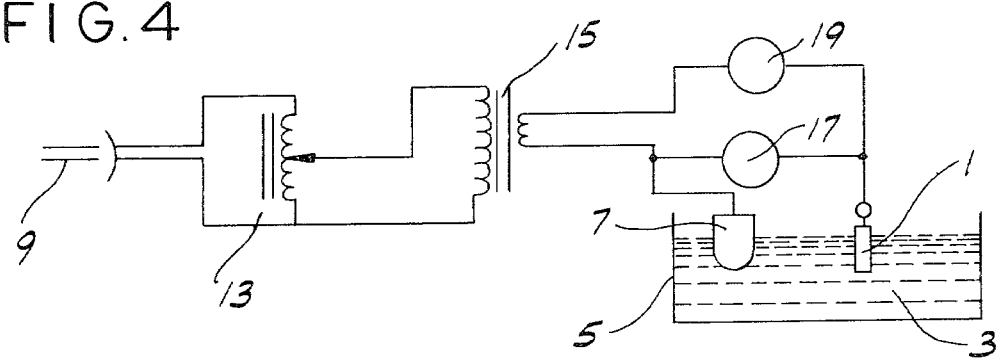
FIG. 4 is a schematic diagram showing the circuit and bath for etching the tip of a wire conductor.

Three lengths of platinum wire approximately 500μ dia.×25 mm long were etched over a portion extending approximately 12 mm from on end thereof in an apparatus of the type illustrated in FIG. 4. The electrochemical etching bath was prepared by dissolving sodium cyanide (57 g) and sodium hydroxide (44 g) in deionized water (150 ml) to provide a solution that was approximately 7.7 M in cyanide ions. Etching was carried out at room temperature at a series of voltages which were progressively decreased so as to form a hemispherical tip at the etched end of each length of wire. At each voltage, each length of wire was alternately dipped in and removed from the electrochemical etching bath in repetitive cycles of 30 seconds in and 30 seconds out. Set forth in Table 1 is the schedule of open circuit potentials (observed at the voltmeter during the portion of each cycle when the wire was removed from the bath and the amperage was zero), the process potential (observed during the portion of the cycle when the wire was immersed in the bath and current was flowing), the process current (observed when the wire was immersed), and the number of cycles at each voltage.

TABLE 1

| Open Circuit Potential(Volts) | Process Potential (Volts) | Process Current(Amps) | # Cycles |
|---|---|---|---|
| 6.5 | 5.0–5.3 | .9–2.5 | 50–60 |
| 5.0 | 4.2 | .5–.8 | 50–60 |
| 3.0 | 2.8 | .1–.3 | 50–60 |
| 1.0 | .95 | .001–.020 | 50–60 |

Prior to etching the lengths of platinum wire were mechanically abraded to roughen their surfaces slightly, thereby promoting subsequent chemical action thereon. After the mechanical abrading step, the wires were cleaned with methyl alcohol, rinsed with distilled water, and then connected to the A.C. power source and immersed in the etching bath. After the etching operation was completed the lengths of wire were removed from the bath, again cleaned with methyl alcohol and rinsed with distilled water.

The etched ends of the lengths of platinum wire were anodized in 1 N sulfuric acid solution. The lengths of wire were connected to the positive terminal of a D.C. voltage source and the etched ends thereof immersed in the sulfuric acid anodizing bath. Formation of an oxide layer was effected by application of a voltage of approximately 2 volts for 15 minutes at room temperature. The anodic oxide layer obtained had a thickness of approximately 100 angstroms. After the anodic oxidation step was complete, the lengths of wire were removed from the sulfuric acid bath and once again rinsed with distilled water to remove residual acid.

Figure 7:
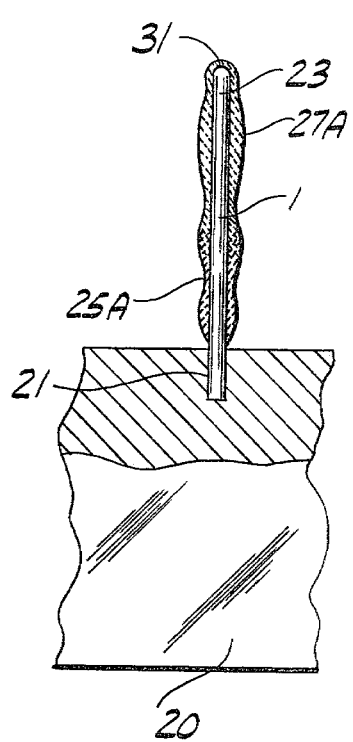

The untreated ends of the anodized, etched lengths of wire were inserted in the wells (5 mm deep) in a Macor ceramic block holder of the type illustrated in FIG. 3 and 5–7. A 5 mm long tube (sleeve) of 0150 insulating glass and a 12 mm long tube of 0120 ion-selective pH glass were thereafter slid over each length of wire as illustrated in FIGS. 6 and 7. The Macor block supporting a number of wire and glass tube assemblies was inserted into an oven and the glass heated rapidly to raise the temperature of the glass to a point at which plastic flow occured so as to seal the ion-selective glass over the upper tip of the platinum wire, provide a low impedance bond between the ion-selective glass and the etched anodized end of the wire, fuse the ion-selective glass tube to the insulating glass, and bond the insulating glass to the wire to provide an insulating jacket surrounding a lower portion of the wire spaced from the etched and anodized end. At the maximum temperature realized, viscosity of the ion-selective glass was low enough so that the membrane at the hemispherical tip of the wire conductor thinned out to a thickness of about 5 microns, thereby providing a very low impedance electrode configuration.

Figure 8:
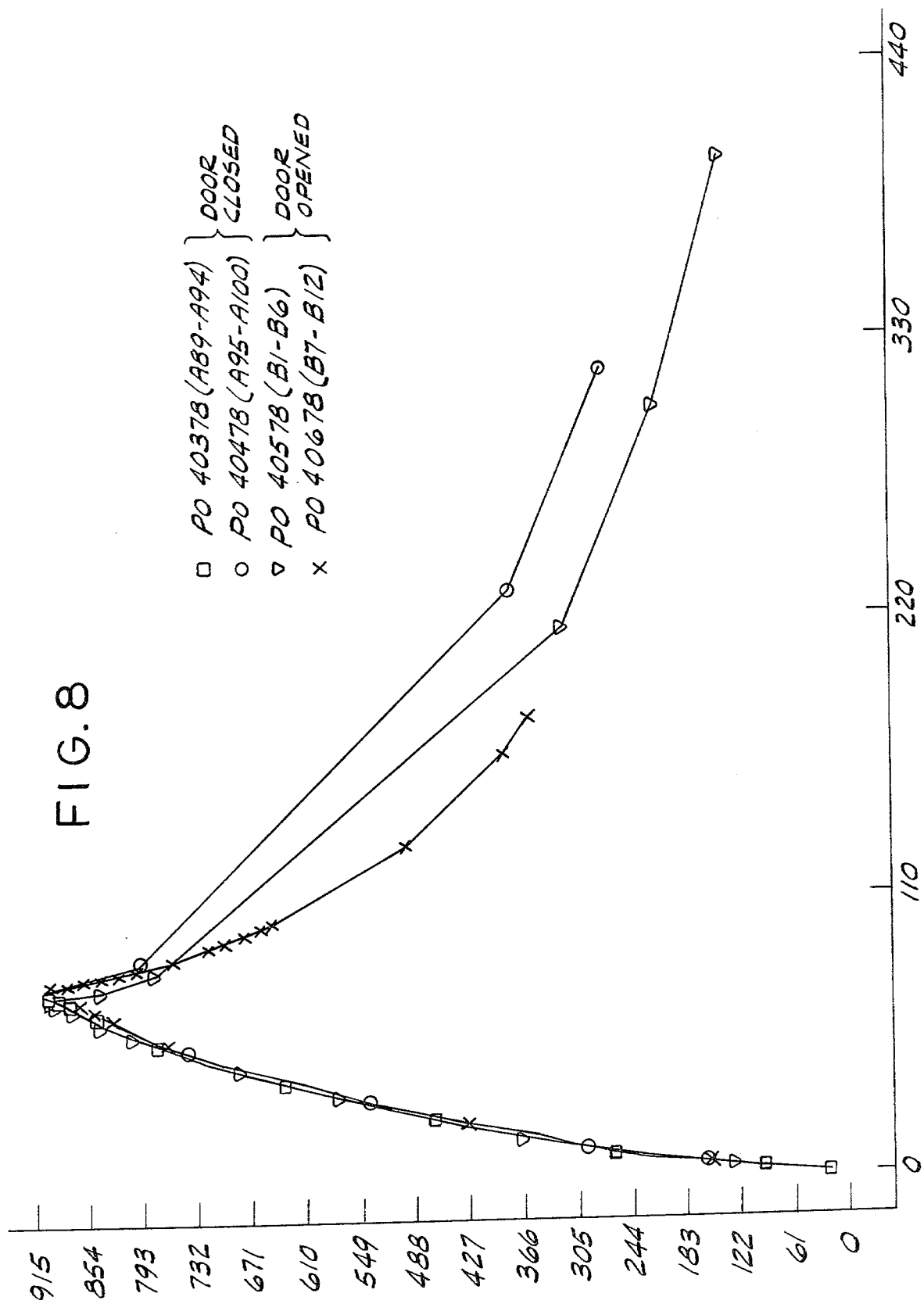
FIG. 8 is a diagram showing the temperature profiles of heat treatment according to the working examples described hereinbelow.

Set forth in FIG. 8 is the temperature profile for both the heating and cooling cycle in the oven. After a temperature of approximately 910° was attained, the glass electrodes were allowed to cool with the oven door closed. After cooling was complete, the electrode holder was removed from the oven, the electrodes were removed from the holder and final assembly steps carried out.

As shown in FIG. 2 the uncoated end of each length of wire (that which extended into well 21 of block 20) was bonded to a conductive lead of a coaxial cable using a silver epoxy adhesive. An epoxy potting compound was then molded around the end of the coaxial cable, the connection between the cable lead and the wire conductor, and the insulating glass jacket of the glass electrode. The epoxy potting compound was also molded around the portion of the ion-selective glass membrane adjacent the insulating jacket so that only the tip of the glass electrode and a short portion of the membrane just inward of the tip remained exposed. The finished product is that illustrated in FIG. 2.

One of the electrodes prepared in accordance with this Example (No. A92) was calibrated for response to pH. The results of the calibration are illustrated in FIG. 9.

EXAMPLE 2

Utilizing the method described in Example 1, six additional platinum in glass dry pH electrodes were prepared. The temperature profile for the heat sealing and glass temperature steps of this example was essentially identical to the profile for Example 1 as shown in FIG. 8. No pH calibration was obtained for this batch of electrodes. They were, however, tested and proven to be pH responsive with a characteristic that appeared similar to that of electrode A92 of Example 1.

EXAMPLE 3

Six additional pH electrodes were prepared utilizing the method described in Example 1 except that the oven door was opened during the cooling cycle and more rapid cooling was achieved. The temperature profile for the heat sealing and glass tempering steps for this example are shown in FIG. 8.

EXAMPLE 4

Six additional pH electrodes were prepared utilizing a method essentially identical to that of Example 3 except that a somewhat steeper cooling curve was realized in the cooling and annealing portion of the heat sealing and glass tempering operation. The temperature profile for the heat treatment step of this example are shown in FIG. 8.

Two of the electrodes prepared in accordance with this example were calibrated for pH. The results of this calibration are shown in FIG. 9. For purposes of comparison, FIG. 9 also shows the calibration curve for a commercially available wet glass electrode sold by Fisher Scientific Co. under the trade designation "Microprobe".

In view of the above, it will be seen that the several objects of the invention are achieved and other advantageous results attained.

As various changes could be made in the above methods and products without departing from the scope of the invention, it is intended that all matter contained in the above description or shown in the accompanying drawings shall be interpreted as illustrative and not in a limiting sense.

What is claimed is:

1. A dry glass electrode for use in potentiometric analysis of aqueous media comprising a metal conductor constituted of a metal selected from the group consisting of platinum, gold, and tantalum, a layer comprising an oxide of said metal having a thickness of between about 50 Angstrom units and about 2 microns on an outer surface of said metal conductor, and an ion-selective glass membrane over and in electrical contact with said oxide layer, said ion-selective glass having a coefficient of thermal expansion differing by less than about 25% from the coefficient of thermal expansion of said metal.

2. An electrode as set forth in claim 1 wherein said glass is an alkali metal glass and said surface of said conductor contains charge transfer promoting amounts of an alkali metal.

3. An electrode as set forth in claim 2 wherein said alkali metal is sodium.

4. An electrode as set forth in claim 1 wherein the conductor comprises a length of wire having said oxide layer on one end thereof and wherein said membrane covers said end.

5. An electrode as set forth in claim 4 wherein the tip of the wire at said end is of substantially hemispherical configuration.

6. An electrode as set forth in claim 4 further comprising a glass insulating jacket fused to said ion-selective glass membrane and surrounding said wire along a portion thereof spaced longitudinally from said tip.

7. An electrode as set forth in claim 6 further comprising a polymeric potting compound surrounding said glass insulating jacket.

8. An electrode as set forth in claim 1 wherein said oxide layer is the product of anodic oxidation of said metal conductor.

9. An electrode as set forth in claim 8 wherein said metal conductor comprises platinum or gold and prior to anodic oxidation said tip is electrolytically etched in an alkaline solution containing cyanide ions and alkali metal ions.

10. An electrode as set forth in claim 1 wherein said ion-selective glass is selective for hydrogen ions so that said electrode constitutes a pH electrode.

* * * * *